(12) United States Patent
Wang

(10) Patent No.: US 7,857,807 B2
(45) Date of Patent: Dec. 28, 2010

(54) INTRA-URETHRAL CATHETERS

(76) Inventor: Dajue Wang, 11 Selkirk Avenue, Aylesbury, Buckinghamshire, HP19 9HP (GB)

( * ) Notice: Subject to any disclaimer, the term of this patent is extended or adjusted under 35 U.S.C. 154(b) by 939 days.

(21) Appl. No.: 10/571,276

(22) PCT Filed: Sep. 10, 2004

(86) PCT No.: PCT/GB2004/003859

§ 371 (c)(1),
(2), (4) Date: Mar. 9, 2006

(87) PCT Pub. No.: WO2005/023353

PCT Pub. Date: Mar. 17, 2005

(65) Prior Publication Data

US 2007/0032780 A1 Feb. 8, 2007

(30) Foreign Application Priority Data

Sep. 10, 2003 (GB) .................................. 0321120.8

(51) Int. Cl.
*A61M 27/00* (2006.01)
(52) U.S. Cl. ......................................... 604/544; 604/19
(58) Field of Classification Search .................. 604/540, 604/541, 542, 543, 544, 19, 43, 93.01, 102.02, 604/102.03, 174, 265; 606/192; 600/29
See application file for complete search history.

(56) References Cited

U.S. PATENT DOCUMENTS

| | | | |
|---|---|---|---|
| 2,642,874 A | 6/1953 | Keeling | |
| 3,769,981 A | 11/1973 | McWhorter | |
| 4,337,775 A | 7/1982 | Cook et al. | |
| 4,589,874 A | 5/1986 | Riedel et al. | |
| 4,878,901 A * | 11/1989 | Sachse | 604/174 |
| 5,007,897 A | 4/1991 | Kalb et al. | |
| 5,591,145 A | 1/1997 | Sachse | |
| 6,080,142 A | 6/2000 | Sachse | |

FOREIGN PATENT DOCUMENTS

| | | |
|---|---|---|
| DE | 2528273 | 10/1976 |
| DE | 3202713 | 8/1983 |
| DE | 41 30 434 A1 | 3/1993 |
| GB | 1 561 569 | 2/1980 |

* cited by examiner

*Primary Examiner*—Loan Thanh
*Assistant Examiner*—Benedict L. Hanrahan
(74) *Attorney, Agent, or Firm*—Davis & Bujold, P.L.L.C.

(57) ABSTRACT

An intra-urethral catheter for a male patient, has a lumen (7) interrupted within the prostatic space (S) of the patient's urethra (U), by a blockage (8), and upper and lower by-pass openings (9, 10) through the catheter-wall (6) are located one above and one below the blockage (8). The upper opening (9) discharges urine collected from the bladder (B) to flush the prostatic space (S), and the lower opening (10) passes the urine back into the lower part (7") of the lumen for discharge. In a modification, the length of the catheter below the sphincter (M) of the bulbar urethra and the external urethral orifice (O), is of membraneous form (11), and at the external urethral orifice (O) extends into a portion (12) for folding back over the glans (G). A ring (13) retains the folded-back portion (12) on the glans (G).

10 Claims, 2 Drawing Sheets

INTRA-URETHRAL CATHETERS

This application is a national stage of PCT/GB2004/003859 filed Sep. 10, 2004 which claims priority from British Application Serial No. 0321120.8 filed Sep. 10, 2003.

FIELD OF THE INVENTION

This invention is concerned with intra-urethral catheters for male patients.

BACKGROUND OF THE INVENTION

According to one aspect of the present invention there is provided a catheter for intra-urethral catheterisation of a male patient, wherein the lumen of the catheter is interrupted within a portion of the catheter that is for positioning within the prostatic part of the patient's urethra during catheterisation, and two by-pass openings through the catheter-wall are located one above and one below the interruption, the upper opening for discharging urine from the upper part of the lumen into the prostatic part of the urethra, and the lower opening for passing the urine from the prostatic part of the urethra into the lower part of the lumen for discharge therefrom.

Secretions from the prostatic part of the urethra are normally flushed away in the flow of urine from the bladder during micturition, but catheterisation using known forms of intra-urethral catheter creates a dead space in which the secretions are retained. Retention of the secretions can readily become a significant source of infection of the bladder, the upper urinary tract, the seminal vesicles, the vas deference, the epididymis and/or the testes. The catheter of the present invention has the advantage that it enables continued flushing away of the secretions, in the urine drained from the bladder, and so allows for catheterisation to be maintained over longer periods than is otherwise possible or prudent with known forms of intra-urethral catheter.

The upper and lower openings are preferably located on opposite sides of the tube from one another so that urine draining from the upper of the two openings flows round the outside of the catheter in returning to the catheter-lumen through the lower opening, and thereby flushes the prostatic part of the urethra more thoroughly than otherwise would be the case. There may, however, be more than one upper opening and/or more than one lower opening in the catheter-wall.

A portion of the length of the catheter that is for positioning within the penile urethra between the bulbar urethra and the external urethral orifice during catheterisation, may be of membraneous form, and at its proximal end for location at the external urethral orifice may extend into a portion for folding back over the glans. The provision of a membraneous portion of this nature has advantages for avoiding discomfort and nuisance often experienced by patients with known catheters where the proximal end of the catheter projects and hangs down from the penis. In this context, moreover, the provision of a membraneous portion is applicable to intra-urethral catheters generally whether or not provision for flushing the prostatic part of the urethra is included.

SUMMARY OF THE INVENTION

Thus, according to another aspect of the invention there is provided a catheter for intra-urethral catheterisation of a male patient, wherein a portion of the length of the catheter that is for positioning within the penile urethra between the bulbar urethra and the external urethral orifice during catheterisation, is of membraneous form, and at its proximal end for location at the external urethral orifice extends into a portion for folding back over the glans.

The membraneous portion of the catheter-length may be of elastic membrane or film, for example latex, and the portion for folding back over the glans may include an elastic ring for retaining it over the glans.

BRIEF DESCRIPTION OF THE DRAWINGS

A catheter for intra-urethral catheterisation of a male patient, in accordance with the present invention will now be described, by way of example, with reference to the accompanying drawings, in which.

DETAILED DESCRIPTION OF THE INVENTION

Figure 1:
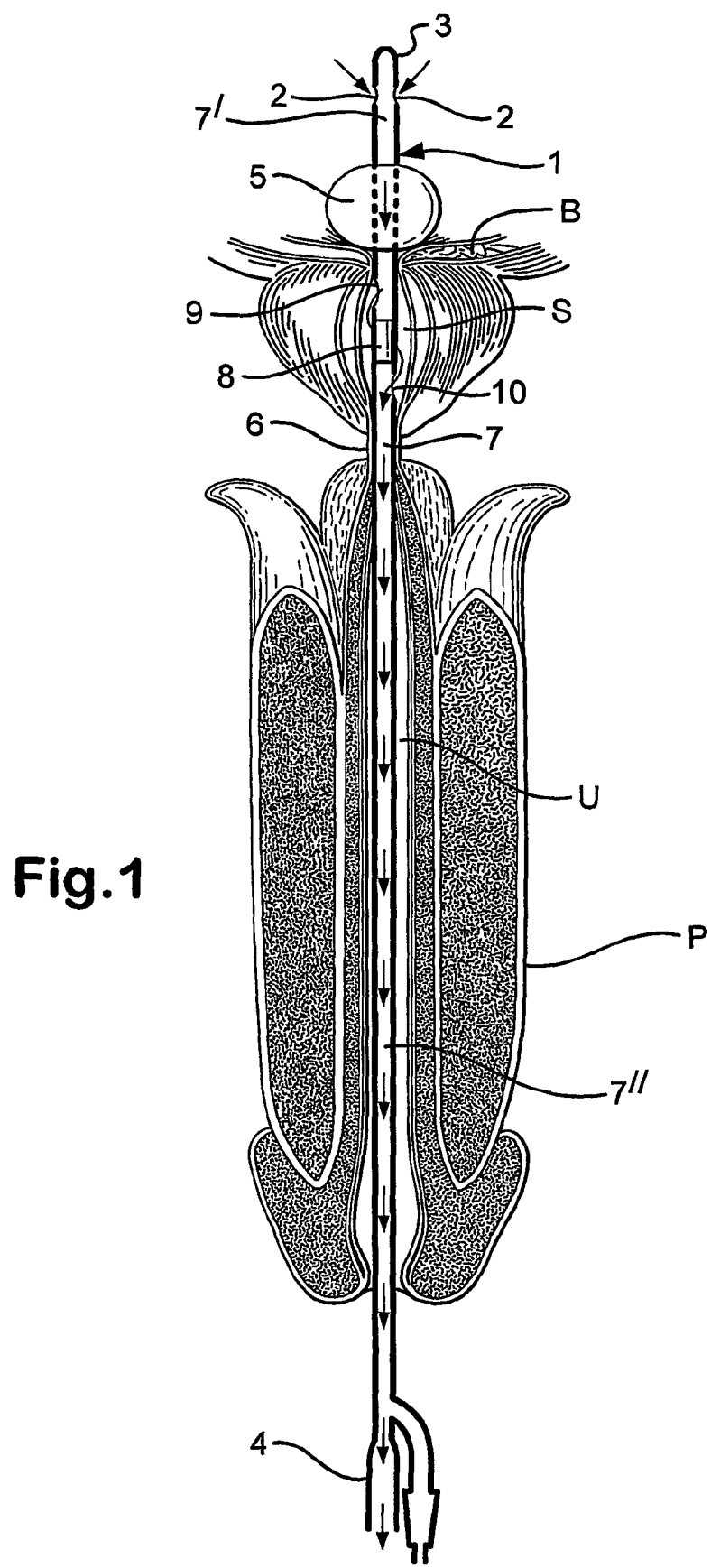
FIG. 1 is a sectional view illustrative of the catheter of the invention during use in the body of a male patient.

Referring to FIG. 1, the intra-urethral catheter of the invention is formed by a tube 1 of plastics material that has side-openings 2 in its otherwise-closed distal tip 3. In the catheterised male patient (as illustrated), the tube 1 extends from its proximal end 4 into the penis P and throughout the length of the urethra U to locate the tip 3 projecting into the patient's bladder B. The catheter is restrained from withdrawal by a balloon 5 which surrounds the tube 1 below the tip 3, and which is inflated within the bladder B through a continuous air-passage (not shown) within the catheter-wall 6.

Urine collecting in the bladder B drains through the openings 2 into the lumen 7 of the indwelling tube 1 for discharge from the proximal end 4 of the catheter. If the catheter were of known form, the lumen 7 would be continuous throughout the length of the tube 1, so that flow of the drained urine would be contained by the tube 1 throughout the length of the urethra U. Thus, secretions within the prostatic space S of the urethra U would not be flushed away as occurs during normal (un-catheterised) micturition, and could readily become a seat of infection, especially during long-term catheterisation.

Figure 2:
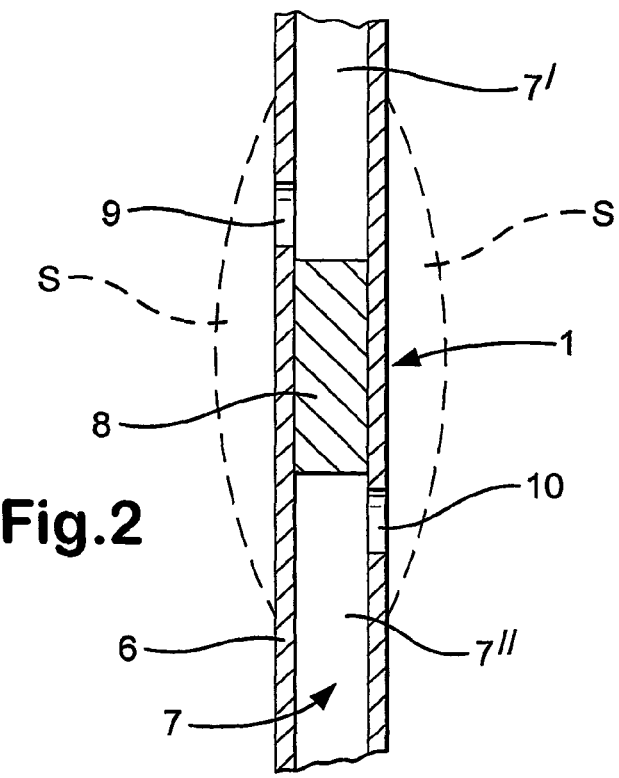
FIG. 2 is an enlarged sectional view of a portion of the catheter-length.

With the catheter of the present invention, the danger of such infection is very significantly reduced by causing the drained urine to flush the space S. To this end, and referring also to FIG. 2, the lumen 7 is interrupted throughout a portion of the catheter-length located within the space S, by a blockage 8 that extends between upper and lower openings 9 and 10 respectively in the wall 6. Urine draining from the bladder B through the openings 2 into the upper part 7' of the lumen 7 is forced to by-pass the blockage 8 by flowing into the space S via the opening 9 and then back into the lower part 7" of the lumen 7, via the opening 10.

The openings 9 and 10 are located on opposite sides of the tube 1 from one another so that the by-pass flow is round the tube 1. The urine drained from the bladder B as a result washes substantially the whole space S, carrying the secretions with it to be discharged from the proximal end 4 of the catheter. The space S within the prostatic part of the urethra (extending for a distance of about 3 cm below the bladder B) is accordingly flushed substantially free from accumulation of secretions, and the risk of infection is reduced.

The blockage 8 may be formed by a length of rod sealed into the lumen 7 of the tube 1, or, more preferably is formed as an integral part of the catheter in manufacture.

With the catheter described above, the proximal end 4 of the catheter projects from the penis P. This can be found to be uncomfortable and a nuisance for the patient especially in those circumstances in which he is mobile independently or in a wheelchair. Indeed, in certain circumstances where the bladder is acontractile, or where it is contractile but not hyperactive, it is not necessary to have retained-connection to the catheter so projection from the penis is unnecessary. The catheter described above can be modified according to another to adapt it to this situation and provide the patient with less nuisance and improved comfort, whilst at the same time maintaining its function of urine-drainage and washing of the prostatic part of the urethra.

Figure 3:
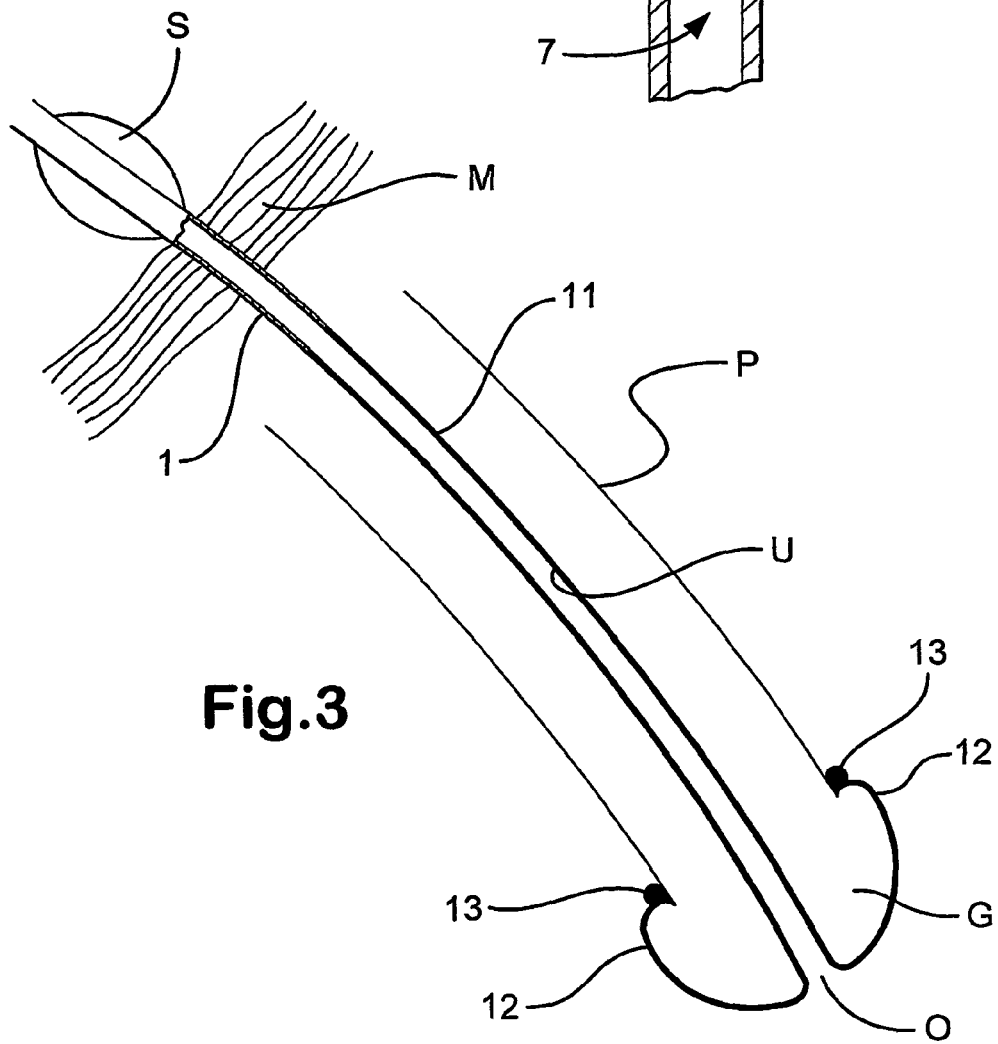
FIG. 3 is illustrative of a modification of the catheter of FIGS. 1 and 2.

In the latter respect, the modification involves shortening the tube 1 so that it extends from just before (that is, proximal to) the bulbar part of the urethra to the bladder. As illustrated in FIG. 3, the removed part of the tube 1 is replaced by a tube 11 of very thin elastic membrane or film (of latex or other material such as used for condoms) which continues the catheter down the urethra U within the penis P to emerge from the external urethral orifice O and fold back over the glans G. The folded-back end 12 of the membraneous-tube 11 terminates in an elastic ring 13 similar to that of a condom, that retains it in place over the surface of the glans G.

The short length of comparatively-solid tube 1 at the distal end of the modified catheter is effective within the bulbar part of the urethra U to hold the sphincter M, open. This allows urine which enters the tube 1 through the openings 2 and flushes the prostatic part of the urethra before entering the lower part 7" of the lumen 7 as described above in connection with FIGS. 1 and 2, to pass and not be blocked by contraction of the muscles of the sphincter M.

Once the urine has passed from the tube 1 within the bulbar part of the urethra into the membraneous-tube 11 there is no other anatomical structure to restrict its flow for discharge as though naturally through the external urethral orifice O.

The use of the membraneous tube 11 has the advantage that nothing projects from the penis P to hang down from it as a potential nuisance or as a source of discomfort. Moreover, the tube 11 has elasticity that allows it to extend with elongation of the penis P during erection.

Considerations that apply to the use and advantages of the catheter of FIG. 3 under various conditions of the patient, are:
(a) In the condition in which the bladder is acontractile but the sphincter is not relaxed, urine cannot pass the barrier of the sphincter even with build up of urine-pressure in the bladder or with the application of safely-moderate external pressure on the abdominal wall or straining. Use of the catheter allows urine to pass the sphincteric barrier under control of the patient applying pressure on the abdominal wall.
(b) In the condition in which the bladder is contractile but not hyperactive, voiding of the bladder is spontaneous though the interval between voidings is sufficiently long and more or less regular. Therefore, the timing of voiding is to a certain extent predictable and controllable depending on the volume of water intake and other factors. The patient has sufficient time to prepare himself for urine drainage and collection.
(c) In the condition in which the bladder is contractile and hyperactive, the spontaneous voiding is frequent, uncontrollable and unpredictable. In such cases, a penile sheath may be attached to the folded-back end 12 of the catheter over the glans, to collect the urine at any time.
(d) In the condition in which compliance of the wall of the bladder is so low (the elasticity of the bladder is damaged), pressure in the bladder cavity may always be higher than atmospheric pressure even if the bladder is acontractile and there is only a small amount of urine in it. As a result, urine flow may be almost constant, and in this case a penile sheath may be attached to the folded-back end 12 of the catheter over the glans for urine-collection.

Where one-off direct collection of urine is necessary, this can be achieved simply by inserting a tube in the tube 11 within the penile urethra. On the other hand where long-term collection is required this can be facilitated by use of a penile sheath attached on top of the fold-back part of the portion 12 as referred to above, regardless of the type of bladder function.

Although the use of the membraneous tube is described above in the context of the catheter of FIGS. 1 and 2 having provision for flushing of the prostatic part of the urethra, its application is not limited to this. It may be used generally for intra-urethral catheters with or without provision for any such flushing.

The invention claimed is:
1. A catheter for intra-urethral catheterisation of a male patient, the catheter comprising:
   an elongate tube having a length to extend throughout the patient's urethra, the tube comprising a tubular wall defining upper and lower lumen-parts of the tube spaced apart along the length of the tube from one another;
   a distal end of the tube for location in the patient's bladder, the distal end having an inlet opening to drain urine from the bladder into the upper lumen-part of the tube, and the distal end of the tube including an inflatable balloon for retention of the distal end of the tube in the patient's bladder;
   a proximal end of the tube for location exiting the patient's penis to discharge urine from the lower lumen-part of the tube; and
   a portion of the length of the tube, extending between the upper and lower lumen-parts of the tube, for location within the prostatic part of the patient's urethra during catheterisation, and the portion of the length of the tube extending between the upper and lower lumen-parts of the tube;
   wherein the tube has an upper by-pass opening through the tubular wall of the tube from the upper lumen-part of the tube, the upper by-pass opening draining urine from the upper-lumen part of the tube into the prostatic part of the patient's urethra to flush secretions from the prostatic part, and a lower by-pass opening through the tubular wall of the tube into the lower lumen-part of the tube, the upper by-pass opening and the lower by-pass opening are configured to be located sufficiently adjacent one another so that, during use of the catheter for intra-urethral catheterisation of a male patient, at least the lower by-pass is accommodated within the prostatic part of the patient's urethra for draining urine carrying the secretions flushed from the prostatic part of the patient's urethra into the lower-lumen part of the tube for discharge from the proximal end of the tube; and
   the tube is sealed closed by a blockage extending throughout the intermediate portion of the length of the tube between the upper by-pass opening and the lower by-pass opening to block passage of urine within the tube between the upper lumen-part and the lower lumen-part of the tube.

2. The catheter according to claim 1, wherein there is only one upper by-pass opening and only one lower by-pass opening, and the upper by-pass opening is located on a first of two opposite sides of the tube, and the lower by-pass opening is located on the second of the two opposite sides of the tube.

3. The catheter according to claim 1, wherein there are a plurality of upper by-pass openings through the tubular wall of the tube from the upper lumen-part of the tube for draining urine from the upper-lumen part of the tube into the prostatic part of the patient's urethra, and a plurality of lower by-pass openings through the tubular wall of the tube into the lower lumen-part of the tube for draining urine from the prostatic part of the patient's urethra into the lower-lumen part of the tube for discharge from the proximal end of the tube.

4. The catheter according to claim 1, wherein the blockage is a length of rod sealed within the intermediate portion of the tube.

5. The catheter according to claim 1 wherein the length of tube includes a membraneous portion for positioning during catheterisation within the patient's penile urethra between the male patient's bulbar urethra and external urethral orifice, the membraneous portion at the external urethral orifice extending to the proximal end of the tube in a membraneous fold-back portion for folding back over the glans of the patient's penis.

6. The catheter according to claim 5, wherein the fold-back portion includes an elastic ring for retaining the fold-back portion folded back over the glands of the patient's penis.

7. The catheter according to claim 5, wherein the membraneous fold-back portion is one of an elastic membrane and membraneous film.

8. The catheter according to claim 5, wherein the membraneous fold-back portion is latex.

9. A catheter in use in intra-urethral catheterisation of a male patient for flushing secretions from a prostatic part of the patient's urethra with urine drained from the patient's bladder, the catheter comprising an elongate tube having a distal end, a proximal end, a tubular wall for defining upper and lower lumen-parts of the tube spaced apart from one another along the length of the tube between the distal and proximal ends, and an intermediate portion of the length of the tube extending between the upper and lower lumen-parts, and the distal end having an inlet opening therein, and wherein the tube has an upper by-pass opening through the tubular wall of the upper lumen-part of the tube and a lower by-pass opening through the tubular wall of the lower lumen-part of the tube, and the tube is sealed closed by a blockage extending throughout the intermediate portion of the length of the tube between the upper by-pass opening and the lower by-pass opening to block passage of urine within the tube between the upper lumen-part and the lower lumen-part of the tube, the upper by-pass opening, the lower by-pass opening and the blockage being located sufficiently adjacent one another so that both the upper by-pass opening and the lower by-pass opening are configured to be positioned within the prostatic part so that the urine from the bladder is only able to flush the prostatic part, and the catheter is located in the patient's urethra during use such that:

(a) the distal end being located in the patient's bladder to drain urine from the patient's bladder into the upper-lumen part of the tube, (b) the upper by-pass opening being located in the prostatic part of the patient's urethra to drain urine from the upper-lumen part of the tube into the prostatic part of the patient's urethra to flush secretions from the prostatic part, and (c) the lower by-pass opening being located in the prostatic part of the patient's urethra to drain urine carrying the secretions from the prostatic part of the patient's urethra into the lower-lumen part of the tube for discharge from the proximal end of the tube, and the upper by-pass and the lower by-pass are located substantially adjacent one another within the prostatic part of the patients urethra so as to prevent any secretion from the prostatic part from reaching the patient's urethra within the penis.

10. A catheter for intra-urethral catheterisation of a male patient, the catheter comprising:

an elongate tube having a length to extend throughout the patient's urethra, the tube comprising a tubular wall defining upper and lower lumen-parts of the tube spaced apart along the length of the tube from one another;

a distal end of the tube for location in the patient's bladder, the distal end having an inlet opening therein for draining urine from the bladder into the upper lumen-part of the tube, and the distal end of the tube including an inflatable balloon to facilitate retention of the distal end of the tube within the bladder of the patient;

a proximal end of the tube for extending from the patient's penis to discharge urine from the lower lumen-part of the tube; and a portion of the length of the tube, extending between the upper and lower lumen-parts of the tube, for location within the prostatic part of the patient's urethra during catheterisation, and the portion of the length of the tube extending between the upper and lower lumen-parts of the tube;

wherein the tube has an upper by-pass opening through the tubular wall of the tube in the upper lumen-part of the tube, the upper by-pass opening facilitates drainage of urine from the upper-lumen part of the tube into the prostatic part of the urethra of the patient to flush secretions from the prostatic part, and a lower by-pass opening through the tubular wall of the tube into the lower lumen-part of the tube, the lower by-pass opening facilitates drainage of urine, carrying the secretions flushed from the prostatic part of the urethra of the patient, into the lower-lumen part of the tube for discharge from the proximal end of the tube;

the tube is sealed closed by a blockage located between the upper by-pass opening and the lower by-pass opening for blocking passage of urine within the tube between the upper lumen-part and the lower lumen-part of the tube; and the upper by-pass and the lower by-pass are configured to be located substantially adjacent one another and substantially adjacent to the balloon so that, during use of the catheter for intra-urethral catheterisation, the upper by-pass and the lower by-pass are both accommodated completely within the prostatic part of the urethra of the patient so as only to flush secretions from the prostatic part and avoid secretions from the prostatic part from flowing along an exterior of the tube toward the distal end.

* * * * *